United States Patent [19]
Lomonossoff

[11] Patent Number: 5,958,422
[45] Date of Patent: *Sep. 28, 1999

[54] MODIFIED PLANT VIRUSES AS VECTORS OF HETEROLOGOUS PEPTIDES

[75] Inventor: George Peter Lomonossoff, Norwich, United Kingdom

[73] Assignee: Axis Genetics PLC, Cambridge, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/612,858

[22] PCT Filed: Jul. 10, 1995

[86] PCT No.: PCT/GB95/01618

§ 371 Date: Jun. 5, 1996

§ 102(e) Date: Jun. 5, 1996

[87] PCT Pub. No.: WO96/02649

PCT Pub. Date: Feb. 1, 1996

[30] Foreign Application Priority Data

Jul. 13, 1994 [GB] United Kingdom .................... 9414118

[51] Int. Cl.[6] .......................... A61K 39/12; C12N 15/64; C12N 5/00; C07H 21/04
[52] U.S. Cl. ...................................... 424/199.1; 435/320.1; 435/419; 435/421; 514/2; 536/23.4; 536/23.6
[58] Field of Search .............................. 424/199.1, 204.1; 435/6, 69.1, 91.4, 320.1, 410, 419, 421; 536/23.4, 23.6; 514/2

[56] References Cited

FOREIGN PATENT DOCUMENTS

| 0174759 | 3/1986 | European Pat. Off. . |
|---|---|---|
| WO89/08145 | 4/1989 | WIPO . |
| WO91/13994 | 9/1991 | WIPO . |
| WO91/15587 | 10/1991 | WIPO . |
| WO92/18618 | 11/1992 | WIPO . |
| WO93/03161 | 2/1993 | WIPO . |
| WO95/21248 | 8/1995 | WIPO . |

OTHER PUBLICATIONS

Chan et al.—Capsid structure and RNA packaging in comoviruses—Seminars in Virology, vol. 1, 1990: pp. 453–466.
Abstract W47–007—Submitted to 8th International Congress of Virology in Berlin in 1990.
Haynes, et al. Development of a genetically–engineered, candidate polio vaccine employingthe self–assembling properties of the tobacco mosaic virus coat protein. Biotechnology, vol. 4:637–641, Jul. 1986.
Evans et al. An engineered poliovirus chimaera elicits broadly reactive HIV–1 neutralizing antibodies. Nature. vol. 339:385–388, Jun. 1, 1989.
Koff et al. Progress and chaooenges toward an AIDS vaccine: Brother can you spare a paradigm? J. Clin. Immunol. vol. 16(3):127–133, Mar. 1996.
Usha et al., "Expression of an Animal Virus Antigenic Site on the Surface of a Plant Virus Particle", Virology 197, (1993) 366–374.
Kennedy et al., "Antiserum to a Synthetic Peptide Recognizes the HTLV–III Envelope Glycoprotein", Science, vol. 231, Mar. 28, 1986, 1556–1559.
Chant and Hoof, "Cowpea Mosaic Virus", CMI/AAB Descriptions of Plant Viruses Aug. 1978, No. 197, (No. 47 revised).
Dessens and Lomonossoff, "Cauliflower mosaic virus 35S promoter–controlled DNA copies of cowpea mosaic virus RNAs are infectious on plants", Journal of General Virology (1993), 74, 889–892.
Sherry et al., "Use of Monoclonal Antibodies to Identify Four Neutralization Immunogens on a Common Cold Picornavirus, Human Rhinovirus 14", Journal of Virology, Jan. 1986, pp. 246–257.
FEBS Letters, vol. 269, No. 1, Aug. 1990, Amsterdam NL, pp. 73–76, Takamatsu, N. et al., "Production of Enkephalin in Tobacco Protoplasts Using Tobacco Mosaic Virus RNA Vector".
Biotechnology, vol. 11, No. 8–93, New York US, pp. 930–932, Hamamoto H., et al. "A New Tobacco Mosaic Virus Vector and its Use for the Systemic Production of Angiotensin–1–Converting Enzyme Inhibitor in Transgenic Tobacco and Tomato".
Virology, vol. 197, 1993, pp. 366–374, Usha R. et al. "Expression of Animal Virus Antigenic Site on the Surface of a Plant Viral Particle" p. 367 Construction of pMT7–FMCV–1 and pMT7–FMDV–II and In Vitro Transcription Reactions.
Virology, vol. 202, Aug. 1, 1994, pp. 949–955, Porta C. et al., "Development of Cowpea Mosiac Virus as a High–Yielding System for the Presentation of Foreign Antigens".
AIDS Research and Human Retroviruses, vol. 11, No. 3, Mar. 1995, pp. 327–334, McLain L. et al., "Human Immunodeficiency Viruses Type 1–Neutralizing Antibodies Raised to a Glycoprotein 41 Peptide Expressed on the Surface of a Plant Virus".
Proceedings of the National Academt of Sciences of USA, vol. 88, Aug. 1991, Washington US, pp. 7204–7208, Donson, J. Et al. "Systemic Expression of a Bacterial Gene by a Tobacco Mosiac Virus–Based Vector".

*Primary Examiner*—James Ketter
*Assistant Examiner*—William Sandals
*Attorney, Agent, or Firm*—McDermott, Will & Emery

[57] ABSTRACT

The invention relates to assembled particles of a plant virus containing a foreign peptide insert in the coat protein of the virus. The site of the insert is free from direct sequence repeats flanking the insert. The invention also relates to a method of production of the particles and their use, in particular in vaccines.

34 Claims, 9 Drawing Sheets

```
  1                     5                    10                    15                   20                    25
  G   P   V   C   A   E   A   S   D   V   Y   S   P   C   M   I   A   S   T   P   P   A   P   F   S
                                                          <------------- βB -------------->
GGACCTGTGTTTGTGCTGAAGCCTCAGATGTGTATAGCCCATGTATGATAGCTAGCTACTCCTCCTGCTCCATTTCA
         2670                                   2700             NheI                    2730

30                      35                       40
  D   V   T   A   V   T   F   D   L   I   N   G   K   I   T
         <--------- βC -------->
GACGTTACAGCAGTAACTTTTGACTTAATCAACGGCAAAATAACT                      (SEQ ID NO:2)
                                        2760                       (SEQ ID NO:1)
```

```
   S  T  Y  S  R  N  A  V  P  N  L  R  G  D  L  Q  V  L  A  Q  K  V  A  R  T  L  P              (SEQ ID NO:4)
CTAGCACTTATATAGTAGAAATGCTGTTCCTAATTTGAGAGGAGATCTTCAAGTTTTGGCTCAAAAGGTTGCTCGGACTCTTC             (SEQ ID NO:3)
GTGAATATCATCTTTACGACAAGGATTAAACTCTCCTCTAGAAGTTCAAAACCGAGTTTTCCAACGAGCCTGAGAAGGATC              (SEQ ID NO:5)
                                           BgIII
```

FIGURE 2(B)

```
   1              5              10             15                                  <----------
   G  P  V  C  A  E  A  S  D  V  Y  S  P  C  M  I  A  S  T  Y  S  R  N  A  V  P  N
GGACCTGTTGTGCTGAAGCCCTAAT GACCCTGTTGTGCTGAAGCCCTAAT... CAGATGTGTATAGCCCCATGTGTATGATAGCTAGCACTTATATAGTAGAAATGCTGTTCCTAAT
    2670                                         2700              NheI
                                                                                             (SEQ ID NO:7)
   --------->                    20                  25
   L  R  G  D  L  Q  V  L  A  Q  K  V  A  R  T  L  P  S  T  P  P  A  P  F  S
TTGAGAGGAGATCTTCAAGTTTTGGCTCAAAAGGTTGCTCGGACTCTTCCTAGCACTCCTCCTGCTCCATTTTCA
     BgIII                                           xNheI                 2730
                                                                                      (SEQ ID NO:6)
```

FIGURE 3

```
        <-------- βB ------->
11                                                              136
 Y  S  P  C  M  I  A  S  T  Y  S  R  N  A  V  P  N  L  R  G  D  L  Q  V  L  A
TATAGCCCATGTATGATAGCTAGCACTTATAGTAGAAATGCTGTTCCTAATTTGAGAGGAGATCTTCAAGTTTTGGCT
ATATCGGGTACATACTATCGATCGTGAATATCATCTTTACGACAAGGATTAAACTCTCCTAGAAGTTCAAAACCGA
                Nhe1                                   Bgl11         (SEQ ID NO:9)

<------ βC ------->
         160              20                30
 Q  K  V  A  R  T  L  P  S  T  P  P  A  P  F  S  D  V  T  A  V  T  F  D  L  I
CAAAAGGTTGCTCGGACTCTTCCTAGCACTCCTGCTCCTCCATTTTCAGACGTTACAGCAGTAACTTTTGACTTAATC
GTTTTCCAACGAGCCTGAGAAGGATCGTGAGGACGAGGAGGTAAAAGTCTGCAATGTCGTCATTGAAAACTGAATTAG
           xNhe1                                        (SEQ ID NO:8)
                                                        (SEQ ID NO:10)
```

FIGURE 5(A)

```
    S  T  D  R  P  E  G  I  E  E  E  G  G  E  R  D  R  D  R  S  D               (SEQ ID NO:16)
CTAGCACTGACCGCCCCTGAGGGCATCGAGGAAGAGGGCGGTGAGCGCGATCGTGATCGTTCGGACGT           (SEQ ID NO:15)
GTGACTGGCGGGGACTCCCGTAGCTCCTTCTCCCGCCACTCGCGCTAGCACTAGCAAGCC                   (SEQ ID NO:17)
                                                   Pvu1
```

FIGURE 5(B)

```
1             5                10                15
G  P  V  C  A  E  A  S  D  V  Y  S  P  C  M  I  A  S  T  D  R  P  E  G  I  E
GGACCTGTGTTTGTGCTGAAGCCTCAGATGTGTATAGCCCATGATAGCACTGACCGCCCCTGAGGGCATCGAG
                                                                    <---------
            2670                        2700          Nhe1

<---------
 E  E  G  G  E  R  D  R  D  R  S  D  V  T  A  V  T  F  D  L  I                 (SEQ ID NO:19)
GAAGAGGGCGGTGAGCGCGATCGTGATCGTTCGGACGTCACAGCAGTAACTTTTGACTTAATC                (SEQ ID NO:18)
                           Pvu1       Aat11
                                    30                  35
                                               2760
```

FIGURE 6(A)

```
    S   T   P   A   T   G   I   D   N   H   R   E   A   K   L   D                    (SEQ ID NO:21)
CTAGCACTCCTGCTACTGGAATCGATAATCATAGAGAAGCTAAAATTGGACGT                                  (SEQ ID NO:20)
                GTGAGGACGATGACCTTAGCTATTAGTATCTCTTCGATTTAACC                           (SEQ ID NO:22)
                          Cla1
```

FIGURE 6(B)

```
     1           5              10                15
     G  P  V  C  A  E  A  S  D  V  Y  S  P  C  M  I  A  S  T  P  A  T  G  I  D  N     <--------
GGACCTGTTTGTGCTGAAGCCTCAGATGTGTATAGCCCATGTATGATAGCTAGCACTCCTGCTACTGGAATCGATAAT
                                                                   Nhe1         Cla1
           2670                          2700

30              35
     H  R  E  A  K  L  D  V  T  A  V  T  F  D  L  I                                    (SEQ ID NO:24)
CATAGAGAAGCTAAATTGGACGTCACAGCAGTAACTTTTGACTTAATC                                       (SEQ ID NO:23)
                     Aat11
                                    2760
    ------->
```

```
                  <------ βB ------->
                              140
11
Y  S  P  C  M  I  A  S     T  V  P  N  L  R  G  D  L  Q  V  L  A
TATAGCCCATGTATGATAGCTAGCACTGTTCCTAATTTGAGAGGAGATCTTCAAGTTTTGGCT
ATATCGGGTACATACTATCGATCGTGACAAGGATTAAACTCTCCTCTAGAAGTTCAAAACCGA
                      NheI                   BglII

<------ βC ------->
                       30
Q  K  V  A  R  T  L  P  D  V  T  A  V  T  F  D  L  I
CAAAAGGTTGCTCGGACTCTTCCTGACGTCACAGCAGTAACTTTTGACTTAATC
GTTTTCCAACGAGCCTGAGAAGGACTGCAGTGTCGTCATTGAAAACTGAATTAG
                       AatII
```

```
160
T  F  D  L  I
TTTGACTTAATC                   (SEQ ID NO:26)
AAACTGAATTAG                   (SEQ ID NO:25)
                               (SEQ ID NO:27)
```

FIGURE 7

```
     20                                                   25
  S  T  P  P  A    (SEQ ID NO:29)                        P  F  S  D      (SEQ ID NO:32)
CTAGCACTCCTCCTGCT  (SEQ ID NO:28)                       CCATTTTCAGACGT  (SEQ ID NO:31)
   GTGAGGAGGACGA   (SEQ ID NO:30)                       GGTAAAAGTC      (SEQ ID NO:33)
```

```
 141
  V  P  N  L  R  G  D  L  Q  V  L  A  Q  K  V  A  R  T  L   (SEQ ID NO:35)
 GTTCCTAATTTGAGAGGAGATCTTCAAGTTTTGGCTCAAAAGGTTGCTCGGACTCTT   (SEQ ID NO:34)
 CAAGGATTAAACTCTCCTCTAGAAGTTCAAAACCGAGTTTTCCAACGAGCCTGAGAA   (SEQ ID NO:36)
```

FMDV-V

```
 85                                        98
  K  D  A  T  G  I  D  N  H  R  E  A  K  L   (SEQ ID NO:38)
 AAAGATGCTACTGGAATCGATAATCATAGAGAAGCAAAATTG   (SEQ ID NO:37)
 TTTCTACGATGACCTTAGCTATTAGTATCTCTTCGTTTTAAC   (SEQ ID NO:39)
```

HRV-II

```
731                                                              752
  P  R  G  P  D  R  P  E  G  I  E  E  E  G  G  E  R  D  R  D  R  S   (SEQ ID NO:41)
 CCTAGAGGACCAGACAGACCTGAAGGAATAGAAGAGGAAGGTGGAGAACGCGATCGAGATAGATCA   (SEQ ID NO:40)
 GGATCTCCTGGTCTGTCTGGACTTCCTTATCTTCTCCTTCCACCTCTTGCGCTAGCTCTATCTAGT   (SEQ ID NO:42)
```

HIV-III

MODIFIED PLANT VIRUSES AS VECTORS OF HETEROLOGOUS PEPTIDES

This invention relates to the use of viruses as carriers (vectors) for the production or presentation of foreign peptides. More particularly, the invention relates to the genetic manipulation of viral nucleic acid by incorporation of foreign nucleic acid sequences which are expressed as peptides in the virus particle (virion). In this specification the term "foreign", as applied to a peptide or to the nucleic acid encoding therefor, signifies peptide or nucleic acid sequences which are not native to the plant virus used as a vector. Such sequences can be alternatively described as exogenous or heterologous sequences. The term "peptide" includes small peptides and polypeptides.

Our patent application WO 92/18618 describes the utilization of plant viruses as vector systems for the expression of foreign nucleotide sequences, ie nucleotide sequences (RNA or DNA) which are not present in plant viruses, as found in Nature, and which in consequence code for peptides not normally found in any naturally occurring plant virus. The invention described therein comprises assembled particles of a plant virus containing a foreign peptide. The plant viruses of the invention are therefore modified forms of the native viruses and for convenience will be referred to as modified viruses.

The foreign peptides which may be incorporated into plant viruses according to our prior application WO92/18618 may be of highly diverse types and are subject only to the limitation that the nature and size of the foreign peptide and the site at which it is placed in or on the virus particle do not interfere with the capacity of the modified virus to assemble when cultured in vitro or in vivo. In broad concept, modified viruses may be formed from any biologically useful peptides (usually polypeptides) the function of which requires a particular conformation for its activity. This may be achieved by association of the peptide with a larger molecule eg to improve its stability or mode of presentation in a particular biological system. Examples of such peptides are peptide hormones; enzymes; growth factors; antigens of protozoal, viral, bacterial, fungal or animal origin; antibodies including anti-idiotypic antibodies; immunoregulators and cytokines, eg interferons and interleukins; receptors; adhesions; and parts of precursors of any of the foregoing types of peptide. The peptide preferably contains more than 5 amino acids.

Among the broad range of bioactive peptide sequences presented on plant virus vectors in accordance with our prior invention special importance attaches to the antigenic peptides which are the basis of vaccines, particularly animal (including human) virus vaccines. It should be noted that in the context of our prior invention vaccines may have prophylactic (ie disease prevention) or therapeutic (ie disease treatment) applications. For vaccine applications our prior invention provides an especially attractive epitope presentation system. When used for such applications the antigenic peptide component will be sited appropriately on the virus particle so as to be easily recognised, by the immune system, for example by location on an exposed part of the coat protein of the virus. As applied to the latter, therefore, our prior invention comprises assembled particles of a modified plant virus containing an antigen derived from a pathogen, eg an animal virus, incorporated in an exposed position on the surface of the coat protein of the plant virus. This invention also comprises the use of such assembled modified plant virus particles as the immunogenic component of a vaccine. Such assembled modified plant virus particles presenting antigenic peptides also have applications as the antigen presentation component of an immunodiagnostic assay for detection of eg animal (including human) pathogens and diseases.

The system described in our prior application is highly versatile in regard to the size of the foreign peptide which may be inserted into the viral coat protein. Thus peptides containing up to 38 or more amino acids have been successfully inserted in the course of our continuing research. However, the modified viruses so produced, being non-natural structures, are at a competitive disadvantage with the unmodified virus (wild type) when propagated in plants. As a result, we have observed a tendency in some modified viruses for the foreign peptide to be lost during propagation with consequent reduction in yield of modified virus.

In accordance with the present invention, the causes of this problem have been identified and the steps necessary to avoid it have been determined.

Firstly, the process used for modifying the plant viral nucleic acid by introducing a nucleotide sequence coding for a foreign peptide should avoid the presence of direct sequence repeats flanking the insert. In the context of the present invention a construct containing a direct sequence repeat is one in which an identical oligonucleotide sequence is present on both sides of the inserted nucleotide. Such constructs can be genetically unstable because recombination can occur between the sequence repeats leading to loss of the foreign peptide coding sequence and reversion to the wild type sequence. Secondly, where the foreign oligonucleotide sequence is inserted into the plant virus genome as a substitution for part of the existing sequence, the resultant modified viral coat protein may be missing in an amino acid sequence which is important for virus replication, encapsidation and spread in the plant. This defect may be readily determined and avoided. Thirdly, the heterologous sequence should not be inserted at a sub-optimal site.

The present invention comprises assembled particles of a plant virus containing a foreign peptide in which the corresponding foreign nucleic acid has been inserted into the plant virus genome in the absence of direct sequence repeats flanking the insert and preferably as an addition to the existing nucleic acid.

In a preferred embodiment the plant virus is cowpea mosaic virus (CPMV) and the foreign insert is made immediately preceding the proline 23 ($Pro^{23}$) residue in the $\beta B$-$\beta C$ loop of the small capsid protein (VP23).

The invention can be applied to any plant virus by identifying that part of the virus genome which encodes an exposed portion of a coat protein. Within this part of the genome two different restriction enzyme sites are chosen and the nucleic acid cleaved using the appropriate restriction enzymes. Pairs of complementary oligonucleotides are synthesised encoding the foreign peptide which it is desired to insert into the virus coat protein. The oligonucleotides terminate in ends which are compatible with the restriction enzyme sites thus allowing insertion into the cleaved virus nucleic acid. This procedure results in the introduction of a nucleotide sequence coding for a foreign peptide whilst avoiding the presence of direct sequence repeats flanking the insert. Preferably complementary oligonucleotides are synthesised in which the sequence encoding the heterologous amino acids are flanked by plant virus-specific sequences so that the foreign nucleic acid is inserted as an addition to the existing nucleic acid.

In a preferred embodiment the three dimensional structure of a plant virus is examined in order to identify portions of a coat protein which are particularly exposed on the virus surface and are therefore potentially optimum sites for insertion. In a further embodiment the amino acid sequence of the exposed portions of a coat protein is examined for amino acids which break α-helical structures because these are potentially optimum sites for insertion. Examples of suitable amino acids are proline and hydroxyproline, both of which whenever they occur in a polypeptide chain interrupt the a herix and create a rigid kink or bend in the structure.

To demonstrate this system, the plant virus cowpea mosaic comovirus (CPMV) was chosen. The three-dimensional structure of CPMV has been solved at atomic resolution which has enabled identification of sites suitable for modification without disruption of the particle structure.

CPMV is a bipartite RNA virus and in order to manipulate the genome of any RNA virus to express foreign peptides it is necessary to use cDNA clones of the RNA. Full length cDNA clones of both CPMV RNA molecules are available which can be manipulated to insert oligonucleotide sequences encoding a foreign peptide. cDNA clones of the genome from plant RNA viruses can be used to generate in vitro transcripts that are infectious when inoculated onto plants. However, the infectivity of the transcripts is significantly lower than that of natural virion RNAs, probably as a result of the presence of non-viral residues at the termini of the transcripts. Difficulties may also be caused by exposure of the transcripts to degradative agents during inoculation. For this reason the transcripts are usually stabilised by capping their 5' ends, but this is an inefficient, costly and time-consuming process.

In a further aspect of the present invention, cDNA clones of CPMV RNAs M and B have been constructed, in which the cDNA clone of the M RNA contains an inserted oligonucleotide sequence encoding a foreign peptide, which make use of the cauliflower mosaic virus (CaMV) 35S promoter sequence linked to the 5' ends of the viral cDNAs to generate infectious transcripts in the plant. This technique overcomes some of the problems encountered with the use of transcripts generated in vitro and is applicable to all plant RNA viruses.

To demonstrate the wide applicability of this invention, antigenic peptides from four different animal viruses, one bacterial pathogen of animals and a mammalian peptide hormone were used. Two of the viruses belong to the picornavirus group of animal viruses—foot and mouth disease virus (FMDV) and human rhinovirus (HRV). There are several important pathogens in this group, particularly, FMDV, poliomyelitis (polio) and hepatitis A. The third virus selected is human immune deficiency virus (HIV) which bears no similarity to any known plant virus, and for which no successful vaccines are currently available. The bacterial pathogen is *Staphylococcus aureus*, a causitive agent of several animals diseases including mastitis in cows. The peptide hormone is porcine gonadotrophin releasing hormone.

The invention will now be further described with reference to the following accompanying drawings:

FIG. 1 depicts the region of CPMV M RNA which encodes the amino-terminal 40 amino acids of VP23. The numbers below the nucleotide sequence refer to the M RNA sequence and the position of the unique Nhe1 site is indicated. The amino acids involved in forming the βB and βC strands of VP23 are indicated above the amino acid sequence of the protein which is shown using the standard one-letter code.

FIG. 2(A) depicts the sequence of the oligonucleotides used in the construction of pFMDV together with the amino acid sequence encoded by the top (positive) strand, which corresponds to amino acid residues 136–160 from VP1 of FMDV serotype $O_1$, and FIG. 2(B) depicts the structure of VP23 after insertion of the FMDV-specific oligonucleotides. The arrowed region indicates the extent of the inserted FMDV epitope. The Nhe1 site not restored during the cloning is indicated by xNhe1. The diagnostic Bg/II site present in the inserted sequence is also indicated.

FIG. 3 depicts the effect of insertion of the FMDV-specific oligonucleotides, encoding amino acid residues 136–160 from VP1 of FMDV serotype $O_1$, on the structure of VP23 in pMT7-FMDV-I. The amino acids involved in forming the βB and βC strands of VP23 are indicated above the amino acid sequence of the protein which is shown using the standard one-letter code.

FIG. 5(A) depicts the nucleotide sequence of the oligonucleotides used in the construction of pMT7-HIV together with the amino acid sequence encoded by the top (positive) strand, which corresponds to amino acid residues 735–752 from gp41 of HIV1, and FIG. 5(B) depicts the structure of VP23 after insertion of the HIV-specific oligonucleotides. The arrowed region indicates the extent of the inserted HIV epitope. The diagnostic Pvu1 site present in the inserted sequence is also indicated.

FIG. 6(A) depicts the nucleotide sequence of the oligonucleotides used in the construction of pMT7-HRV together with the amino acid sequence encoded by the top (positive) strand which corresponds to amino acid residues 85–99 from VP1 of HRV-14, and FIG. 6(B) depicts the sequence of VP23 after insertion of the HRV-specific oligonucleotides. The arrowed region indicates the extent of the inserted HRV epitope. The diagnostic Cla1 site present in the inserted sequence is also indicated.

FIG. 7 depicts the effect of insertion of the FMDV-specific oligonucleotides, (depicted in bold type) encoding amino acid residues 141–160 from VP1 of FMDV serotype $O_1$, on the sequence of VP23 in pMT7-FMDV-II.

FIG. 8: Sequence of the oligonucleotides used to construct pMT7-FMDV-V, pMT7-HRV-II and pMT7-HIV-III. All oligonucleotides used terminated in the sequences shown in bold at the top of the diagram. The variable portions used for the construction of pMT7-FMDV-V (FMDV-V), pMT7-HRV-II (HRV-II) and pMT7-HIV-III (HIV-III) are shown below. The amino acid sequences encoded by the plus-sense oligonucleotides are indicated above the nucleotide sequence and correspond as follows: FMDV-V, amino acids 141–160 from VP1 of FMDV serotype $O_1$; HRV-II amino acids 85–98 from VP1 of HRV-14; HIV-III, amino acids 731–752 from gp41 of HIV-I.

Figure 9:
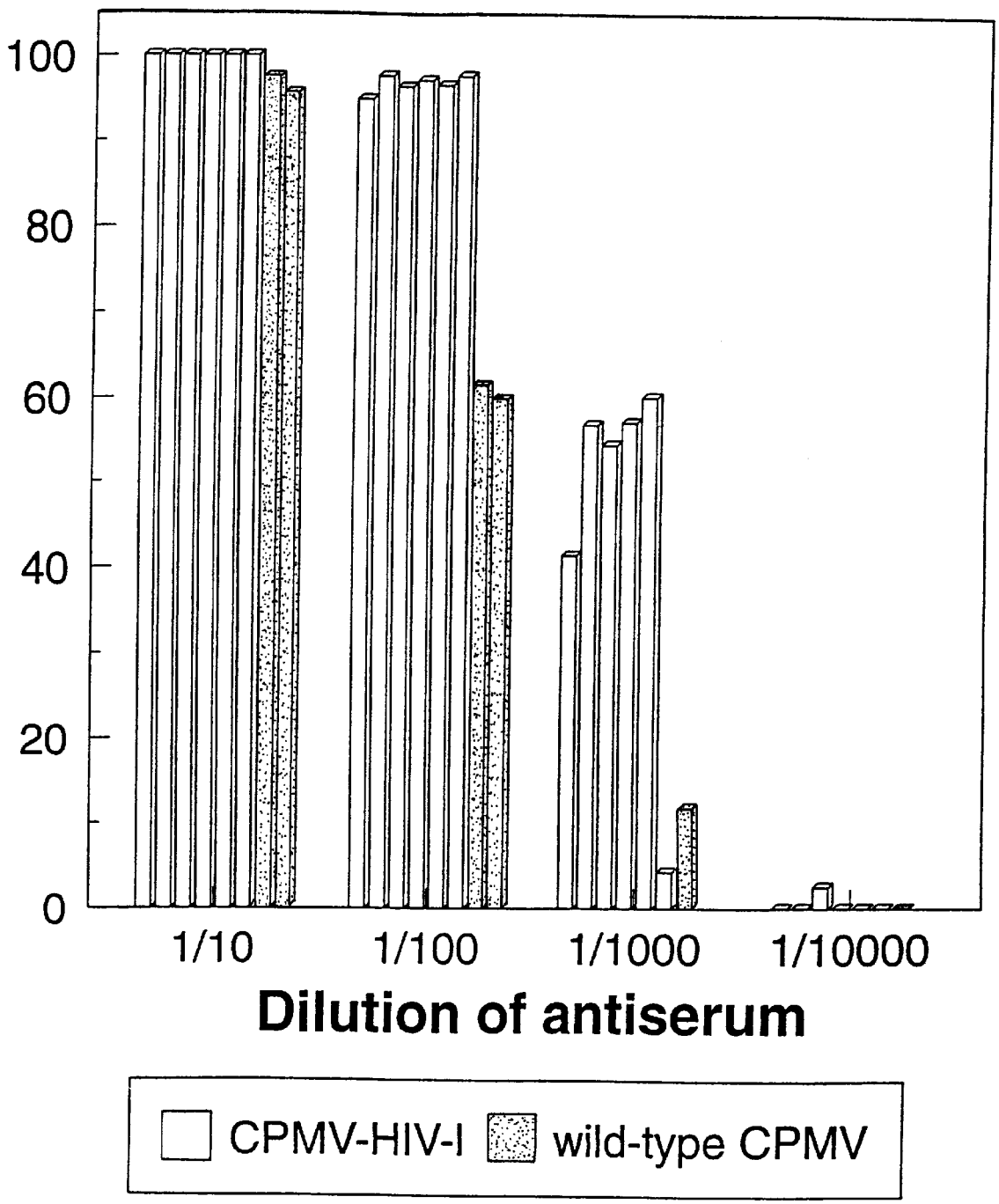

FIG. 9: Neutralization of HIV-1 IIIB by sera from individual C57/BL6 mice given two subcutaneous injections of the CPMV-HIV-I chimaera expressing amino acids 731–752 of gp41 on its surface (open bars). Mice were bled after 14 days. Also shown is the mean serum neutralization titre of a parallel group of mice inoculated with wild type CPMV (solid bars). All immunogens were formulated in alum adjuvant.

MODIFICATION OF CPMV

Methods for manipulating the genome of the virus in order to make insertions into the coat protein of CPMV are described in WO 92/18618. A full length cDNA clone of CPMV M RNA in the transcription vector pPMI is available (pPMM2902), as is a full length cDNA clone of CPMV B RNA (pBT7-123). A mixture of transcripts from pPMM2902 and pBT7-123 gives rise to a full virus infection when electroporated into cowpea protoplasts.

We have selected the βB-βC loop in VP23 for the insertion of foreign peptide. This loop is clearly exposed on the surface of the viral particle and computer modelling has shown that even large loops inserted at this site are unlikely to interfere with the interaction between adjacent subunits responsible for capsid structure and stability. This loop has a unique Nhe1 site at position 2708 of the M RNA-specific sequence where foreign sequences may be inserted (see FIG. 1).

The principal antigenic sites of the picornavirus foot and mouth disease (FMDV) and human rhinovirus (HRV), and the lentiretrovirus human immune deficiency virus (HIV) were used to illustrate the use of modified plant viruses in the production of vaccines to animal viruses.

The design and construction of pFMDV, a full length cDNA clone of CPMV M RNA containing a DNA insert coding for a segment of FMDV loop protein, is described in WO 92/18618. An oligonucleotide sequence encoding amino acid residues 136–160 from VP1 of FMDV serotype $O_1$, strain BFS 1860 was inserted into the unique Nhe1 site of pPMM2902 as an addition to the existing nucleic acid. The procedure used resulted in the creation of a direct repeat sequence flanking the insert (see FIG. 2B). The properties of pFMDV transcripts are described in WO 92/18618. Infection of cowpea protoplasts with a mixture of pFMDV and pBT7-123 transcripts leads to multiplication and assembly of modified virus particles.

However, to produce modified plant viruses on a large scale it is necessary to prepare a construct which can be inoculated directly onto whole plants, and which will replicate and assemble into virus particles as in the protoplast system. Therefore pPMM2902 was modified such that RNA synthesis is driven by a more efficient promoter and the modified plasmid transcribed under conditions that result in the transcripts having a "cap" structure at their 5' ends. The steps in the modification of pPMM2902 to produce pMT7-601 are described in detail in WO 92/18618. A mixture of capped pMT7-601 and pBT7-123 transcripts was found to be infectious to intact cowpea plants.

The design and construction of pMT7-FMDV-I, starting from pMT7-601 and pFMDV, are described in WO 92/18618. An oligonucleotide sequence encoding amino acid residues 136–160 from VP1 of FMDV serotype $O_1$, was inserted into the unique Nhe1 site of pMT7-601 as an addition to the existing nucleic acid. The procedure used resulted in the creation of a direct repeat sequence flanking the insert (see FIG. 3). The properties of pMT7-FMDV-I transcripts are described in detail in Usha et al [Virology (1993) 197, 366–374]. Plants inoculated with a mixture of pMT7-FMDV-I and pBT7-123 transcripts developed lesions on their inoculated leaves which were smaller than those seen on the leaves of plants inoculated with wild type transcripts. Immunosorbent electron microscopy on leaf homogenates from inoculated leaves of pMT7-FMDV-I-infected plants confirmed the presence of CPMV-like virus particles. However, there was no evidence of systemic spread of the chimaeric virus particles to uninoculated leaves.

We have since characterised the progeny of a pMT7-FMDV-I infection by reverse transcriptasepolymerase chain reaction (RT-PCR) analysis of RNA extracted from leaves inoculated with pMT7-FMDV-I. The analysis revealed the presence of two products, the major one corresponding to the expected product of approximately 580 bp and a minor one of 500 bp . The latter product comigrated with the product synthesised from RNA extracted from a plant infected with wild-type CPMV. When the PCR products were cloned into bacteriophage M13 and the sequence around the site of insertion was determined, two classes of clones could be found: those which retained the entire FMDV-specific sequence (the majority) and those which contained a sequence corresponding exactly to wild-type CPMV (the minority). These results indicate that reversion to the wild-type sequence occurs in the transcript-inoculated leaves by an apparently single-step process.

When RNA extracted from a pMT7-FMDV-I transcript-inoculated leaf was passaged on to uninfected cowpeas, the plants developed symptoms on their inoculated leaves which consisted of a mixture of small lesions characteristic of a pMT7-FMDV-I infection and larger wild-type CPMV lesions. In addition, the upper leaves developed mosaic symptoms characteristic of a wild-type CPMV infection. RT-PCR analysis of RNA extracted from the inoculated leaves of such plants again yielded two products but in this case the dominant one corresponded to that derived from wild-type M RNA. Analysis of clones derived from the dominant mixture of PCR products again revealed the same two classes of sequence found previously. However, in this case the majority of clones represented the wild-type sequence. These results indicate that not only does pMT7-FMDV-I tend to lose the entire FMDV-specific sequence in a single step process, probably as a result of the presence of direct repeats flanking the insert but also that wild-type progeny virus has a significant advantage over the chimaeric virus.

Figure 4:
FIG. 4 depicts the construction of a "substitution" vector by site-directed mutagenesis. The asterisk indicates the T residue that is changed to a C by site-directed mutagenesis, thereby creating a novel AatII site.

In order to avoid the creation of a direct repeat sequence flanking the insert, a second restriction enzyme cutting site was created in the nucleotide sequence of the region of the CPMV genome encoding VP23. A single silent base change (U to C) at position 2740 of the M RNA creates a unique AatII site at amino acid valine 27 (position 2735 of the nucleotide sequence). This was achieved by site-directed mutagenesis of M13-JR-1 using methods described in WO 92/18618 (see FIG. 4). The creation of the AatII site enables the nucleotide sequence encoding the six amino acids from the native βB-βC loop in CPMV to be removed by digestion with NheI and AatII. The sequence can then be replaced by any sequence with NheI- and AatII-compatible ends.

Construction of pMT7-FMDV-II, pMT7-HIV and pMT7-HRV

Three different sequences were designed to be substituted for the sequence between the NheI and AatII sites of the mutated M RNA sequence. In all three cases the foreign sequences substituted for wild-type sequences encoding six amino acids. The first sequence to be substituted into VP23 consisted of oligonucleotides encoding residues 735–752 from the transmembrane glycoprotein gp41 from human immunodeficiency virus (HIV-1). This sequence was selected because a synthetic peptide for this region is recognised in enzyme-linked immunosorbent assays (ELISA) by antisera from seropositive AIDS patients and is capable of inducing antibodies which neutralise a range of HIV-1 isolates. The second sequence consists of the nucleotide sequence encoding residues 85–99 from VP1 of human rhinovirus 14 (HRV-14). In both cases, the oligonucleotides were designed to contain restriction enzyme sites to facilitate screening. The sequences of the oligonucleotides and the effect of the substitutions on the amino acid sequence of VP23 are shown in FIGS. 5 and 6. The methods used for the construction of pMT7-HIV and pMT7-HRV are given in WO 92/18618.

The third sequence consisted of nucleotides encoding residues 141–160 from VP1 of FMDV serotype $O_1$. The effect of the substitution on the amino acid sequence of VP23 is shown in FIG. 7. The method used for the construction of pMT7-FMDV-II is given in Usha et al (1993).

The properties of pMT7-HIV and pMT7-FMDV-II transcripts are described in WO 92/18618 and Usha et al (1993) respectively. pMT7-HIV transcripts, when mixed with pBT7-123 transcripts can replicate in cowpea protoplasts and the resultant modified coat protein can assemble into chimaeric virus particles. Similarly, pMT7-FMDV-II transcripts can replicate in cowpea protoplasts but progeny RNA accumulated at a considerably lower level than that from pMT7FMDV-I, or from pMT7-601 which contains the wild-type VP23 sequence. No virus particles could be detected in protoplasts infected with pMT7-FMDV-II. The ability of transcripts derived from pMT7-FMDV-II to multiply in whole cowpea plants was also studied by Usha et al (1993).

No symptoms developed on inoculated plants and no progeny RNA could be detected in either the inoculated or the upper leaves. The reduced infectivity of pMT7-FMDV-II may be attributed to the resultant chimaeric virus particles lacking an amino acid sequence which is present in the wild type virus, and in chimaeric virus produced from pMT7-FMDV-I infections, and is important for virus replication and spread in the plant.

EXAMPLE 1

Construction of pMT7-FMDV-V, pMT7-HRV-II and pMT7-HIV-III

The small lesion phenotype of pMT7-FMDV-I and its competitive disadvantage in comparison with wild-type CPMV, suggest that the heterologous sequence may have been inserted at a sub-optimal site. Detailed examination of the 3-D structure of CPMV revealed that proline 23 ($Pro^{23}$), which lies in the centre of the βB-βC loop of the S protein, is particularly exposed on the virus surface and is potentially the optimum site for any insertion. To make use of this fact and to prevent the introduction of repeated sequences which may facilitate reversion, pairs of complementary oligonucleotides were synthesised in which the sequence encoding the heterologous amino acids are flanked by sequences present in wild type CPMV such that the insert is made immediately preceeding $Pro^{23}$. The oligonucleotides terminate in NheI and AatII-compatible ends enabling them to be inserted between the NheI and AaflI sites of either pMT7-FMDV-II (Usha et al, 1993) or its derivative pMT7-FMDV-II AatII in place of the original FMDV-specific insert. Such a strategy not only ensures that the heterologous sequences are inserted at the optimal site and that the inserts are not flanked by direct repeats but also ensures that no CPMV-specific sequences are deleted, a fact believed to be important in enabling virus particles to assemble (Usha et al, 1993). The sequences inserted in this manner consisted of residues 141–160 of VP1 of FMDV serotype $O_1$ (a slightly shorter version of the epitope in pMT7-FMDV-1), residues 85–98 of VP1 of HRV-14 which make up the immunodominant site, NIm-IA [Sherry et al, J. Virology, (1986) 57, 246–257], and an epitope comprising residues 731–752 from gp41 of HIV-1, the so-called "Kennedy epitope" [Kennedy et al, Science, (1986) 231, 1556–1559]. The sequence of the oligonucleotides used in the constructions is shown in FIG. 8. The resulting constructs were designated pMT7-FMDV-V, pMT7-HRV-II and pMT7-HIV-III, respectively.

The construction and properties of plasmids pBT7-123, pMT7-FMDV-I and pMT7-FMDV-II have been described previously (Usha et al, 1993). These constructs and their derivatives were propagated in *Escherichia coli* strain JM83. Oligonucleotides were synthesised on a Pharmacia Gene Assembler Plus synthesiser. Sequence analysis was performed by "dideoxy" method using either *E. coli* DNA polymerase I (Klenow fragment) or SEQUENASE™ version 2.0.

To construct pMT7-FMDV-V, pMT7-FMDV-II was digested to completion with NheI (which cleaves at position 2708 of the M RNA sequence) and partially with AatII which cuts once within the M RNA sequence (position 2735) and once in the pUC-derived portion of the plasmid (position 2617 on the pUC19 map). A pair of complementary oligonucleotides encoding residues 141–159 from VP1 of FMDV serotype $O_1$, flanked by sequences encoding residues 18–22 and 23–26 of the CPMV VP23 protein (FIG. 8) were phosphorylated, annealed and ligated into NheI/AatII-digested pMT7-FMDV-II. Recombinants having the desired structure were identified by restriction enzyme mapping and sequence analysis.

To construct pMT7-HRV-II and pMT7-HIV-III, pMT7-FMDV-II was initially partially digested with AatII and full-length linear molecules recovered after agarose gel electrophoresis. The linearised plasmid was treated with *E. coli* DNA polymerase I (Klenow fragment) to remove the 3' overhangs left by AatII, recircularised and transformed back into *E. coli* strain JM83. A recombinant, designated pMT7-FMDV-AatII, in which the AatII site in the pUC portion of the plasmid had been destroyed but which retained the AatII site in the M RNA specific portion was identified by restriction enzyme analysis. Complementary oligonucleotides encoding residues 85–98 from VP1 of HRV-14 or residues 731–752 of gp41 of HIV-I, flanked by the appropriate CPMV-specific sequences were phosphorylated, annealed and ligated into NheII/AatII-digested pMT7-FMDV-AatII giving rise to pMT7-HRV-II and pMT7-HIV-III, respectively.

EXAMPLE 2

Ability of pMT7-FMDV-V, pMT7-HRV-II and pMT7-HIV-III to Replicate in Whole Cowpea Plants When RNA was transcribed from the chimaeric plasmids, mixed with transcripts from pBT7-123 and inoculated on to cowpea plants, in each case the inoculated leaves developed chlorotic lesions typical of a wild-type CPMV infection. RNA hybridisation analysis revealed the presence of M RNA-specific sequences within these leaves. In all three cases the infection could be mechanically transmitted to further healthy cowpea plants. In the case of pMT7-HRV-II and pMT7-HIV-III the infection spread to the upper leaves of most of the infected plants giving a typical systemic mosaic. However, the infection induced by pMT7-FMDV-V remained associated exclusively with the inoculated leaves, no systemic symptoms being observed and no viral-specific RNA being detected in the upper leaves of the plants.

When total RNA was extracted from leaves inoculated with pMT7-FMDV-V transcripts and analysed by RT-PCR, only a single band corresponding in size to the product derived from RNA retaining the insert was observed. Even after up to three serial passages, a similar result was obtained. To confirm that the insert had been retained, the products derived from samples taken from plants after initial inoculation and after three serial passages were cloned into bacteriophage M13 and the nucleotide sequence of a representative number of clones determined. All the clones in both instances contained the sequence corresponding to viral RNA which retained the inserted sequence intact. These results indicate that reversion of pMT7-FMDV-V RNA had not occurred at a detectable frequency. Analysis of RNA extracted from purified pMT7-HRV-II and pMT7-HIV-III particles (see below) supported the conclusion that the new constructs are genetically stable, no evidence of reversion being found after 10 serial passages.

Virus particles could be prepared from leaf tissue infected with either pMT7-HRV-II or pMT7-HIV-III using the standard CPMV purification protocol [van Kammen and de Jager, (1978), Cowpea mosaic virus. CMI/AAB Descriptions of Plant Viruses, 197], the yields obtained (1.2–1.5 mg of virus per gram of fresh tissue) being similar to that obtained with wild-type CPMV. By contrast no particles derived from pMT7-FMDV-V could be obtained using the standard procedure or a number of variants of it. This failure was not due to the absence of particles within the infected tissue since large numbers of such particles could be seen by immunosorbent electron microscopy (ISEM) of tissue homogenate using grids coated with anti-CPMV serum.

EXAMPLE 3
Immunological Properties of Chimaeric Virus Particles Derived from pMT7-HRV-II and pMT7HIV-III To confirm that the purified pMT7-HRV-II particles possessed the antigenic properties of the inserted sequence, samples of the purified virions were subjected to western blot analysis using a polyclonal antiserum raised against HRV-14. A product corresponding in size to the modified VP23 protein could be detected, confirming the antigenicity of the inserted sequence. No reaction could be seen with the antiserum when samples of wild-type CPMV were analysed in the same way.

When a sample of denatured virus was examined by electrophoresis on a SDS-polyacrylamide gel, only three bands were seen. The largest polypeptide (L) corresponds to the large (VP37) viral coat protein and comigrated with the L polypeptide from wild-type CPMV. The middle band ($S_S$) corresponds to the small (VP23) viral coat protein harbouring the HIV-1-specific epitope. The fastest migrating band (S') represents the C-terminal 192 amino acids of the VP23 protein. Terminal sequence analysis showed that it was derived from the VP23 protein by proteolytic cleavage between the two C-terminal amino acid residues of the insert. Thus $S_S$, but not S', contains the insert and as predicted reacts with gp41-specific antibody by Western blotting. The predicted N-terminal cleavage product consists of only 43 residues and could not be resolved on the gel system used. Both elements of S remain associated with the virion. Because a certain amount of S' protein was always present in preparations of CPMV-HIV regardless of how quickly the virus was purified, it is possible that this cleavage occurs in planta.

The strategy designed to overcome the limitations of pMT7-FMDV-I has proved to be successful since all three of the new chimaeras (pMT7-FMDV-V, pMT7-HRV-II and pMT7-HIV-III) gave wild-type symptoms on the inoculated leaves and showed no sign of reversion. Furthermore, two of the chimaeras grew as well as wild-type CPMV and could be readily purified. The fact that pMT7-FMDV-V gives wild-type lesions on inoculated leaves but fails to spread systemically suggests that these chimaeric virus particles are fully competent for cell-to-cell movement but deficient for long-distant transport. This phenomenon may be related to the observation that particles from pMT7-FMDV-V appear to aggregate into intracellular crystalline arrays making purification problematic. These features are not a result of the length of heterologous sequence since pMT7-FMDV-V contains an insert intermediate in size (19 residues) between those contained in pMT7-HRV-II (14 residues) and pMT7-HIV-III (22 residues).

EXAMPLE 4
Use of Chimaeric pMT7-HRV-II Virus Particles to Raise Antibodies to HRV Particles of pMT7-HRV-II and wild-type CPMV were purified as described in Example 2, injected into rabbits, the antisera collected and used to probe western blots of denatured HRV-14 virus particles. A single band corresponding to VP1 of HRV-14 could be detected using the antiserum raised against pMT7-HRV-II virus particles even when the serum was diluted 1:16,000. No reaction could be seen with the other HRV-14 coat proteins (VP2 and VP3). No reaction with any HRV-14 protein was found when serum raised against wild-type CPMV was used to probe the blots. The ability of pMT7-HRV-II virions to raise antibodies which recognise VP1 of HRV-14 shows that epitopes presented on the surface of CPMV particles are immunogenic.

EXAMPLE 5
Use of Chimaeric pMT7-HIV-III Virus Particles to Raise Neutralizing Antibodies to HIV Transcripts derived from pMT7-HIV-III were mixed with transcripts derived from plasmid pBT7-123 and inoculated onto the leaves of 10 day-old cowpea plants. To obtain large yields of recombinant virus particles, samples of leaf tissue showing symptoms characteristic of a CPMV infection were homogenised in 100 mM sodium phosphate pH7.0, centrifuged briefly and the supernatant used to inoculate healthy cowpea plants. The plants were harvested 2–3 weeks post-inoculation and chimaeric virus particles purified as described in Example 2. The purified chimaeric virus, designated CPMV-HIV-I, was stored at 4° C. in 10 mM sodium phosphate pH7.0 in the presence of 0.05% (w/v) sodium azide. The quality of the preparation was monitored by electron microscopy and by electrophoresis of portions of denatured virus on 15% polyacrylamide/SDS/reducing gels. The proteins were visualised by staining the gel with coomassie brilliant blue R250. Prior to injection into mice the virus preparation was dialysed against phosphate-buffered saline and protein concentration determined by Bio-Rad™ assay.

Adult C57/BL6 mice were immunized at 8 weeks of age. Virus (CPMV-HIV-I or CPMV) was mixed with aluminium hydroxide adjuvant at a ratio of 1:5 with stirring for 30 min at room temperature. Mice (6 per group) were immunized subcutaneously at the back of the neck in 5 sites with a total of 100 µl of virus-adjuvant mixture containing 100 µg virus. At the required intervals animals were bled from the tail, and serum stored at −20° C. All sera were heated at 56° C. for 30 min before being assayed for neutralizing antibody.

Mice were given two injections of CPMV-HIV-I or wild type CPMV at 0 and 35 days and bled from the tail 14 days later. Individual neutralizing titres to HIV-1IIIB were then determined as follows. Dilutions of heat-treated serum were incubated with about 2000 syncytium-forming units (sfu) per ml of virus for 1 h at 37° C. Semiconfluent monolayers of C8166 cells (5×10⁴ cells/well) were prepared in 96-well tissue culture plates, which had been pretreated with poly-L-lysine. Medium was removed and the cells received 50 µl of inoculum. These were incubated for 1 h at 37° C. before fresh medium was added. Incubation was continued for 3 days at 37° C., and synctia were then counted with the aid of a microscope and the percentage inhibition calculated for each well.

FIG. 9 shows that neutralising antibody was produced in mice immunised with CPMV-HIV-I with a 50% neutralizing titre of about ¹⁄₁₀₀₀ in 83% of the mice. Antiserum diluted ¹⁄₁₀₀ gave a mean neutralisation titre of 97% with 100% mice responding. The response was highly uniform. FIG. 9 also shows that a control group injected in parallel with wild type CPMV also gave a neutralizing response to HIV-1. The neutralisation titre was about 10-fold lower than with CPMV-HIV-I with a 50% neutralization titre of was about ¹⁄₁₀₀. This was evidently a de novo antibody response as there was no significant neutralization with serum from non-immunized litter mates even at a dilution of ¹⁄₁₀.

The stability of the neutralizing antibody response to the CPMV-HIV chimaera was investigated by bleeding the mice again at 48 days after the second injection. These antisera had no significant neutralizing titre at a dilution of 1/10, indicating that the level of neutralizing antibody had declined by over 100-fold. The neutralizing activity stimulated by wild type CPMV was now also undetectable.

The same mice were given a third injection of CPMV-HIV-I as before, 3 months after the second injection, and bled 14 days later. The mean neutralization titre was 54% at a 1/1000 dilution with all mice now responding. There was no neutralization at this dilution with serum from mice boosted with wild type CPMV. Thus there was little overall increase in neutralising activity. The stability of the neutralizing antibody response to CPMV-HIV-I was checked with antiserum obtained after 56 days. The titres had fallen but antisera from all mice still gave significant neutralization at a dilution of 1/10, with a mean value of 58%. Neutralization by antisera from controls inoculated with wild type CPMV was barely significant.

Neutralization of the homologous HIV-1 strain IIIB by antiserum obtained after the third injection was compared with the neutralization of HIV-1 strains RF and SF2. At a dilution at which strain IIIB was neutralized by 92%, RF was neutralized by 78%, and SF2 by 66%. Antisera made against wild type CPMV also neutralised all three strains, but relative to strain IIIB these antisera neutralised RF and SF2 less than antisera raised against CPMV-HIV-I.

It was confirmed that the neutralizing antibodies in the antiserum made against the wild type CPMV were all specific for CPMV epitopes, with none made against the HIV-1 gp41 peptide, by adsorbing antisera with purified wild type CPMV. Three successive adsorptions with CPMV did not significantly reduce the HIV-1 neutralizing titre of the anti-CPMV-HIV-I serum but reduced the neutralising titre of the anti-CPMV serum 5-fold. Thus we conclude that the majority of neutralizing antibodies made against the CPMV-HIV chimaera were made against HIV-specific epitopes, but that CPMV stimulates antibodies that cross-react with neutralising epitopes of HIV-I.

EXAMPLE 6

Construction of cDNA Clones of CPMV RNA M and B which Can Be Used to Directly Inoculate Plants.

cDNA clones of RNAs M and B of CPMV were constructed in pUC18 such that the 5' ends of the viral RNAs are abutted directly to the transcriptional start site of the CaMV 35S promoter. In addition, the RNA B clone (pCP1) can be linearised precisely at the 3' end of the viral sequence by restriction enzyme digestion at a unique MluI site and the RNA M clone (pCP2) can be treated similarly with Eco RI. Therefore, after digestion with these enzymes, run-off transcripts can be generated which contain no non-viral sequences at either their 5' or 3' ends.

The clones were constructed as described in Dessens et al [Journal of General Virology (1993) 74, 889–892]. The CaMV 35S promoter was cloned between the HindIII and PstI sites of pUC18, during which process the HindIII site was lost. This promotor sequence is flanked by SstII and StuI restriction sites, the latter of which allows blunt-end digestion to expose the transcriptional start site. cDNAs were generated for RNAs M and B and the 5' halves of these were cloned independently by digestion with SstI and BamHI respectively and ligation into a StuI/SstI- or StuI/BamHI-cut CaMV 35S vector. The 3' halves of the RNAs were cloned into these constructs by utilising previously constructed cDNA clones (pMT7-601 and pBT7-123) which had been engineered such that the 3' ends could be precisely exposed by restriction enzyme digestion. RNA M was cloned on a PstI/EcoRI fragment and RNA B on a BglII/EcoRI fragment.

The CaMV 35S promotor utilises host plant DNA dependent RNA polymerases and is highly active. Therefore an infection can be generated in the plant host simply by abrading the surface of the primary leaves in the presence of a mixture of linearised pCP1 and pCP2. The host polymerase directs transcription of viral RNA from the CaMV 35S promotor in vivo, and in cells where both pCP1 and pCP2 are transcribed, an infection similar to that obtained with wild type CPMV is generated. Therefore an in vitro RNA transcription step is no longer required. This represents a considerable advantage over the previous method for inoculating plants both in termrs of ease of use and cost.

In order to allow the production of assembled particles of CPMV containing a foreign peptide which has been inserted immediately preceeding the Pro$^{23}$ residue in the βB-βC loop of the small capsid protein, and in which the corresponding foreign nucleic acid has been inserted into the CPMV genome in the absence of direct sequence repeats flanking the insert and as an addition to the existing nucleic acid, cDNA clone pCP2 was mutated as described for pMT7 earlier in this specification to create a unique AatII site at position 2735 of the RNA M sequence. This was designated pCP2-AatII.

Oligonucleotide sequences encoding various foreign peptides (see Table 1) were substituted for the sequence between the Nhe1 and AatII sites of pCP2-AatII as described in Example 1. The pCP2-AatII variants and pCP-1 were linearised and inoculated onto the primary leaves of cowpea plants. In all cases infections developed and stable chimaeric virus particles expressing the appropriate foreign peptide were recovered from plants.

TABLE 1

Foreign peptide sequences expressed as chimaeric virus particles produced by direction inoculation of plants with cDNA clones

| CONSTRUCT | LENGTH (amino acids) | PEPTIDE SOURCE |
| --- | --- | --- |
| HIV-1 | 22 | amino acids 731–752 of gp41 of HIV-I strain IIIB |
| HIV-3 | 6 | amino acids 312–317 of gp120 of HIV-I strain IIIB (the V3 loop) |
| HIV-4 | 11 | amino acids 140–150 of gp120 of HIV-I strain IIIB (the V1 loop) |
| HIV-5 | 11 | amino acids 117–127 of gp120 of HIV-I strain IIIB |
| FMDV-5 | 19 | amino acids 141–159 of VP1 of FMDV strain $O_1$ (the G-H loop) |
| FMDV-12 | 21 | A peptide sequence from VP1 of FMDV strain CS8 (the G-H loop) |
| FMDV-13 | 23 | A peptide sequence from VP1 of FMDV strain A10 (the G-H loop) |
| FMDV-14 | 10 | amino acids 40–49 of VP1 of FMDV strain $O_1$ (the B-C loop) |
| PARVO-1 | 17 | amino acids 13–29 of VP2 of canine parvovirus |
| PARVO-2 | 17 | the insert sequence of PARVO-1 in reverse |
| PARVO-3 | 17 | a flanking sequence variant of PARVO-1 |
| GNRH-1 | 10 | an immunodominant epitope from pig gonadotrophin releasing hormone |
| MAST-1 | 30 | derived from the fibronectin binding protein of *Staphylococcus aureus* |
| MAST-2 | 38 | a longer version of MAST-1 |
| HRV-2 | 14 | amino acids 85–98 of VP1 of HRV strain 14 |

I claim:

1. Assembled particles of a plant virus containing a foreign peptide insert as an addition at a non-terminal site in the coat protein of the virus, the site of the insert in the coat protein corresponding to a site in the plant virus genome which is free from direct nucleotide sequence repeats flanking the insert and wherein the coat protein of the virus has a β-barrel structure and the site of insertion of the foreign peptide is in a loop connecting β sheets of the plant virus, wherein the plant virus is a comovirus.

2. Virus particles according to claim 1, wherein the foreign peptide is inserted next to a proline or hydroxyproline residue in a loop connecting β sheets of the plant virus.

3. Virus particles according to claim 1, in which the comovirus is cowpea mosaic virus (CPMV).

4. Virus particles according to claim 1, in which the foreign peptide is inserted in the βB-βC loop of the plant virus.

5. Virus particles according to claim 1, in which the foreign peptide is a biologically functional peptide, the biological application of which requires or is enhanced by presentation of the peptide in association with a larger molecule or particle.

6. Virus particles according to claim 1 or 5, in which the foreign peptide is incorporated in an exposed surface of the coat protein of the plant virus.

7. Virus particles according to claim 1 or 5, wherein the plant virus is an RNA virus.

8. Virus particles according to claim 1, in which the foreign peptide is an animal virus antigen derived from foot and mouth disease virus (FMDV).

9. Virus particles according to claim 1 or 3 to 4, in which the foreign peptide is an animal virus antigen derived from human immune deficiency virus (HIV).

10. Virus particles according to any of claims 1 or 3 to 4, in which the foreign peptide is an animal virus antigen derived from a human rhinovirus (HRV).

11. Virus particles according to any of claims 1 or 3 to 4, in which the foreign peptide is an animal virus antigen derived from canine parvovirus.

12. Virus particles according to claim 1 or 5, in which the foreign peptide is an animal pathogen antigen derived from *Staphylococcus aureus*.

13. Virus particles according to claim 1 or 5, in which the foreign peptide is an antigen derived from a peptide hormone.

14. Virus particles according to claim 13, in which the foreign peptide is an antigen derived from gonadotrophin releasing hormone.

15. Virus particles according to claim 1 or 5, in which the peptide is an antigen.

16. Virus particles according to claim 15, in which the antigen is a viral antigen.

17. Virus particles according to claim 16, in which the antigen is an animal viral antigen.

18. An animal virus antigenic complex comprising virus particles according to claim 17 as an immunogenic component thereof.

19. A method of protecting animals against pathogens which comprises administering to said animals the antigenic complex of claim 18.

20. An antigenic complex comprising assembled plant virus particles according to claim 15 as an immunogenic component thereof.

21. A method of protecting animals against pathogens which comprises administering to said animals (including humans) the antigenic complex of claim 20.

22. A method of producing plant virus particles according to any of claims 1 or 5, which comprises inserting a nucleotide sequence coding for a foreign peptide into the virus genome of the plant viral nucleic acid which codes for the coat protein so as to modify the plant viral nucleic acid in such a way as to avoid the production of direct sequence repeats flanking the introduced sequence, infecting plants, plant tissue, plant cells, or protoplasts with the modified viral nucleic acid, and harvesting assembled particles of said plant virus.

23. A method according to claim 22, in which the nucleotide sequence is inserted in that part of the plant viral nucleic acid which codes for an exposed portion of the coat protein.

24. A method according to any of claims 22, in which the foreign nucleotide sequence is inserted by selecting two different restriction enzyme sites in the plant viral nucleic acid; cutting the plant viral nucleic acid using the corresponding restriction enzymes; and inserting into the cut viral nucleic acid a pair of complementary oligonucleotides which encode the foreign peptide and which terminate in ends compatible with the restriction enzyme cutting sites, and wherein in the complementary oligonucleotides, the sequence encoding the foreign peptide is flanked by plant virus-specific sequences so that the foreign nucleotide sequence is inserted as an addition to the plant viral nucleic acid.

25. A method according to claim 22, applied to an RNA plant virus, which comprises introducing a DNA sequence coding for the foreign peptide into a cDNA corresponding to the RNA of the plant virus which codes for an exposed portion of its coat protein, producing from the thus modified cDNA an RNA transcript thereof, inoculating plants, plant tissue, plant cells, or protoplasts with the transcript, optionally together with any other RNA required for multiplication and assembly of whole virus particles in the plant material, and harvesting assembled particles of the modified virus.

26. A method according to claim 25, in which the modified cDNA is produced by introducing the DNA encoding the foreign peptide into a DNA fragment excised from the plant viral cDNA, and recombining the modified fragment so as to reconstitute the plant viral cDNA in modified form.

27. A method according to claim 23, in which modified virus produced, or RNA extracted therefrom, is passaged in plants to produce further yields of modified virus.

28. A method according to claim 25 in which the cDNA contains a cauliflower mosaic virus 35S promoter sequence linked to the 5' end of the nucleotide sequence.

29. A fragment of a CPMV coat protein cDNA containing a DNA sequence which encodes a foreign peptide, said cDNA encoding said foreign peptide corresponding to a site in the CPMV genome which is free from direct nucleotide sequence repeats flanking the DNA encoding the foreign peptide.

30. A fragment according to claim 29, being an Sst1 fragment.

31. A vector containing a fragment according to claim 29.

32. A vector comprising a full length cDNA of CPMV M RNA containing a DNA insert encoding a foreign peptide at a site corresponding to an exposed surface of the coat protein of CPMV, the site being free from direct sequence repeats flanking the DNA insert.

33. An RNA transcript of the fragment of CPMV coat protein cDNA of claim 29 or 30 or RNA transcript of the vector of claim 31 or 32.

34. A capped RNA transcript according to claim 33.

* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 120 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..120

(xi) SEQUENCE DESCRIPTION: SEQ ID NO:1:

```
GGA CCT GTT TGT GCT GAA GCC TCA GAT GTG TAT AGC CCA TGT ATG ATA        48
Gly Pro Val Cys Ala Glu Ala Ser Asp Val Tyr Ser Pro Cys Met Ile
 1               5                  10                  15

GCT AGC ACT CCT CCT GCT CCA TTT TCA GAC GTT ACA GCA GTA ACT TTT        96
Ala Ser Thr Pro Pro Ala Pro Phe Ser Asp Val Thr Ala Val Thr Phe
                20                  25                  30

GAC TTA ATC AAC GGC AAA ATA ACT                                       120
Asp Leu Ile Asn Gly Lys Ile Thr
            35                  40
```

(2) INFORMATION FOR SEQ ID NO:2:

(i) SEQUENCE CHARACTERISTICS:
      (A) LENGTH: 40 amino acids
      (B) TYPE: amino acid
      (D) TOPOLOGY: linear (ii) MOLECULE TYPE: protein (xi) SEQUENCE DESCRIPTION: SEQ ID NO:2:

```
Gly Pro Val Cys Ala Glu Ala Ser Asp Val Tyr Ser Pro Cys Met Ile
 1               5                  10                  15

Ala Ser Thr Pro Pro Ala Pro Phe Ser Asp Val Thr Ala Val Thr Phe
                20                  25                  30

Asp Leu Ile Asn Gly Lys Ile Thr
            35                  40
```

(2) INFORMATION FOR SEQ ID NO:3:

(i) SEQUENCE CHARACTERISTICS:
      (A) LENGTH: 81 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

```
CTAGCACTTA TAGTAGAAAT GCTGTTCCTA ATTTGAGAGG AGATCTTCAA GTTTTGGCTC      60

AAAAGGTTGC TCGGACTCTT C                                               81
```

(2) INFORMATION FOR SEQ ID NO:4:

(i) SEQUENCE CHARACTERISTICS:
      (A) LENGTH: 27 amino acids
      (B) TYPE: amino acid (C) STRANDEDNESS: single
            (D) TOPOLOGY: linear (ii) MOLECULE TYPE: protein (xi) SEQUENCE DESCRIPTION: SEQ ID NO:4:

Ser Thr Tyr Ser Arg Asn Ala Val Pro Asn Leu Arg Gly Asp Leu Gln
1               5                   10                  15

Val Leu Ala Gln Lys Val Ala Arg Thr Leu Pro
            20                  25

(2) INFORMATION FOR SEQ ID NO:5:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GTGAATATCA TCTTTACGAC AAGGATTAAA CTCTCCTCTA GAAGTTCAAA ACCGAGTTTT           60

CCAACGAGCC TGAGAAGGAT C                                                    81

(2) INFORMATION FOR SEQ ID NO:6:

(i) SEQUENCE CHARACTERISTICS:
            (A) LENGTH: 156 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..156

(xi) SEQUENCE DESCRIPTION: SEQ ID NO:6:

GGA CCT GTT TGT GCT GAA GCC TCA GAT GTG TAT AGC CCA TGT ATG ATA            48
Gly Pro Val Cys Ala Glu Ala Ser Asp Val Tyr Ser Pro Cys Met Ile
                    45                  50                  55

GCT AGC ACT TAT AGT AGA AAT GCT GTT CCT AAT TTG AGA GGA GAT CTT            96
Ala Ser Thr Tyr Ser Arg Asn Ala Val Pro Asn Leu Arg Gly Asp Leu
                60                  65                  70

CAA GTT TTG GCT CAA AAG GTT GCT CGG ACT CTT CCT AGC ACT CCT CCT           144
Gln Val Leu Ala Gln Lys Val Ala Arg Thr Leu Pro Ser Thr Pro Pro
            75                  80                  85

GCT CCA TTT TCA                                                           156
Ala Pro Phe Ser
        90

(2) INFORMATION FOR SEQ ID NO:7:

(i) SEQUENCE CHARACTERISTICS:
            (A) LENGTH: 52 amino acids
            (B) TYPE: amino acid
            (D) TOPOLOGY: linear (ii) MOLECULE TYPE: protein (xi) SEQUENCE DESCRIPTION: SEQ ID NO:7:

Gly Pro Val Cys Ala Glu Ala Ser Asp Val Tyr Ser Pro Cys Met Ile
1               5                   10                  15

Ala Ser Thr Tyr Ser Arg Asn Ala Val Pro Asn Leu Arg Gly Asp Leu
            20                  25                  30

```
Gln Val Leu Ala Gln Lys Val Ala Arg Thr Leu Pro Ser Thr Pro Pro
         35                  40                  45

Ala Pro Phe Ser
         50

(2) INFORMATION FOR SEQ ID NO:8:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..156

(xi) SEQUENCE DESCRIPTION: SEQ ID NO:8:

TAT AGC CCA TGT ATG ATA GCT AGC ACT TAT AGT AGA AAT GCT GTT CCT        48
Tyr Ser Pro Cys Met Ile Ala Ser Thr Tyr Ser Arg Asn Ala Val Pro
         55                  60                  65

AAT TTG AGA GGA GAT CTT CAA GTT TTG GCT CAA AAG GTT GCT CGG ACT        96
Asn Leu Arg Gly Asp Leu Gln Val Leu Ala Gln Lys Val Ala Arg Thr
         70                  75                  80

CTT CCT AGC ACT CCT CCT GCT CCA TTT TCA GAC GTT ACA GCA GTA ACT       144
Leu Pro Ser Thr Pro Pro Ala Pro Phe Ser Asp Val Thr Ala Val Thr
 85                  90                  95                 100

TTT GAC TTA ATC                                                       156
Phe Asp Leu Ile (2) INFORMATION FOR SEQ ID NO:9:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:9:

Tyr Ser Pro Cys Met Ile Ala Ser Thr Tyr Ser Arg Asn Ala Val Pro
 1               5                  10                  15

Asn Leu Arg Gly Asp Leu Gln Val Leu Ala Gln Lys Val Ala Arg Thr
             20                  25                  30

Leu Pro Ser Thr Pro Pro Ala Pro Phe Ser Asp Val Thr Ala Val Thr
         35                  40                  45

Phe Asp Leu Ile
         50

(2) INFORMATION FOR SEQ ID NO:10:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATATCGGGTA CATACTATCG ATCGTGAATA TCATCTTTAC GACAAGGATT AAACTCTCCT      60

CTAGAAGTTC AAAACCGAGT TTTCCAACGA GCCTGAGAAG GATCGTGAGG AGGACGAGGT     120
```

```
AAAAGTCTGC AATGTCGTCA TTGAAAACTG AATTAG                                    156
```

(2) INFORMATION FOR SEQ ID NO:11:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..69

(xi) SEQUENCE DESCRIPTION: SEQ ID NO:11:

```
CCA TGT ATG ATA GCT AGC ACT CCT CCT GCT CCA TTT TCA GAC GTT ACA            48
Pro Cys Met Ile Ala Ser Thr Pro Pro Ala Pro Phe Ser Asp Val Thr
             55                  60                  65

GCA GTA ACT TTT GAC TTA ATC                                                69
Ala Val Thr Phe Asp Leu Ile
     70                  75
```

(2) INFORMATION FOR SEQ ID NO:12:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:12:

```
Pro Cys Met Ile Ala Ser Thr Pro Pro Ala Pro Phe Ser Asp Val Thr
  1               5                  10                  15

Ala Val Thr Phe Asp Leu Ile
             20
```

(2) INFORMATION FOR SEQ ID NO:13:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..69

(xi) SEQUENCE DESCRIPTION: SEQ ID NO:13:

```
CCA TGT ATG ATA GCT AGC ACT CCT CCT GCT CCA TTT TCA GAC GTC ACA            48
Pro Cys Met Ile Ala Ser Thr Pro Pro Ala Pro Phe Ser Asp Val Thr
             25                  30                  35

GCA GTA ACT TTT GAC TTA ATC                                                69
Ala Val Thr Phe Asp Leu Ile
 40                  45
```

(2) INFORMATION FOR SEQ ID NO:14:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:14:

Pro Cys Met Ile Ala Ser Thr Pro Pro Ala Pro Phe Ser Asp Val Thr
 1               5                  10                  15
Ala Val Thr Phe Asp Leu Ile
            20

(2) INFORMATION FOR SEQ ID NO:15:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..65

(xi) SEQUENCE DESCRIPTION: SEQ ID NO:15:

CT AGC ACT GAC CGC CCT GAG GGC ATC GAG GAA GAG GGC GGT GAG CGC      47
   Ser Thr Asp Arg Pro Glu Gly Ile Glu Glu Glu Gly Gly Glu Arg
        25                  30                  35

GAT CGT GAT CGT TCG GAC GT                                          67
Asp Arg Asp Arg Ser Asp
    40

(2) INFORMATION FOR SEQ ID NO:16:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:16:

Ser Thr Asp Arg Pro Glu Gly Ile Glu Glu Glu Gly Gly Glu Arg Asp
 1               5                  10                  15
Arg Asp Arg Ser Asp
            20

(2) INFORMATION FOR SEQ ID NO:17:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GTGACTGGCG GGACTCCCGT AGCTCCTTCT CCCGCCACTC GCGCTAGCAC TAGCAAGCC    59

(2) INFORMATION FOR SEQ ID NO:18:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..141

(xi) SEQUENCE DESCRIPTION: SEQ ID NO:18:

```
GGA CCT GTT TGT GCT GAA GCC TCA GAT GTG TAT AGC CCA TGT ATG ATA          48
Gly Pro Val Cys Ala Glu Ala Ser Asp Val Tyr Ser Pro Cys Met Ile
            25                  30                  35

GCT AGC ACT GAC CGC CCT GAG GGC ATC GAG GAA GAG GGC GGT GAG CGC          96
Ala Ser Thr Asp Arg Pro Glu Gly Ile Glu Glu Glu Gly Gly Glu Arg
        40                  45                  50

GAT CGT GAT CGT TCG GAC GTC ACA GCA GTA ACT TTT GAC TTA ATC             141
Asp Arg Asp Arg Ser Asp Val Thr Ala Val Thr Phe Asp Leu Ile
 55                  60                  65
```

(2) INFORMATION FOR SEQ ID NO:19:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO:19:

```
Gly Pro Val Cys Ala Glu Ala Ser Asp Val Tyr Ser Pro Cys Met Ile
 1               5                  10                  15

Ala Ser Thr Asp Arg Pro Glu Gly Ile Glu Glu Glu Gly Gly Glu Arg
                20                  25                  30

Asp Arg Asp Arg Ser Asp Val Thr Ala Val Thr Phe Asp Leu Ile
         35                  40                  45
```

(2) INFORMATION FOR SEQ ID NO:20:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..50

(xi) SEQUENCE DESCRIPTION: SEQ ID NO:20:

```
CT AGC ACT CCT GCT ACT GGA ATC GAT AAT CAT AGA GAA GCT AAA TTG           47
   Ser Thr Pro Ala Thr Gly Ile Asp Asn His Arg Glu Ala Lys Leu
            50                  55                  60

GAC GT                                                                    52
Asp
```

(2) INFORMATION FOR SEQ ID NO:21:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:21:

```
Ser Thr Pro Ala Thr Gly Ile Asp Asn His Arg Glu Ala Lys Leu Asp
 1               5                  10                  15
```

(2) INFORMATION FOR SEQ ID NO:22:

(i) SEQUENCE CHARACTERISTICS:
        (A) LENGTH: 44 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GTGAGGACGA TGACCTTAGC TATTAGTATC TCTTCGATTT AACC                                44

(2) INFORMATION FOR SEQ ID NO:23:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..126

(xi) SEQUENCE DESCRIPTION: SEQ ID NO:23:

GGA CCT GTT TGT GCT GAA GCC TCA GAT GTG TAT AGC CCA TGT ATG ATA                48
Gly Pro Val Cys Ala Glu Ala Ser Asp Val Tyr Ser Pro Cys Met Ile
            20                  25                  30

GCT AGC ACT CCT GCT ACT GGA ATC GAT AAT CAT AGA GAA GCT AAA TTG                96
Ala Ser Thr Pro Ala Thr Gly Ile Asp Asn His Arg Glu Ala Lys Leu
        35                  40                  45

GAC GTC ACA GCA GTA ACT TTT GAC TTA ATC                                       126
Asp Val Thr Ala Val Thr Phe Asp Leu Ile
    50                  55

(2) INFORMATION FOR SEQ ID NO:24:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:24:

Gly Pro Val Cys Ala Glu Ala Ser Asp Val Tyr Ser Pro Cys Met Ile
 1               5                  10                  15

Ala Ser Thr Pro Ala Thr Gly Ile Asp Asn His Arg Glu Ala Lys Leu
             20                  25                  30

Asp Val Thr Ala Val Thr Phe Asp Leu Ile
             35                  40

(2) INFORMATION FOR SEQ ID NO:25:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..117

(xi) SEQUENCE DESCRIPTION: SEQ ID NO:25:

TAT AGC CCA TGT ATG ATA GCT AGC ACT GTT CCT AAT TTG AGA GGA GAT                48
Tyr Ser Pro Cys Met Ile Ala Ser Thr Val Pro Asn Leu Arg Gly Asp
            45                  50                  55

```
CTT CAA GTT TTG GCT CAA AAG GTT GCT CGG ACT CTT CCT GAC GTC ACA        96
Leu Gln Val Leu Ala Gln Lys Val Ala Arg Thr Leu Pro Asp Val Thr
        60                  65                  70

GCA GTA ACT TTT GAC TTA ATC                                           117
Ala Val Thr Phe Asp Leu Ile
 75              80
```

(2) INFORMATION FOR SEQ ID NO:26:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:26:

```
Tyr Ser Pro Cys Met Ile Ala Ser Thr Val Pro Asn Leu Arg Gly Asp
 1               5                  10                  15

Leu Gln Val Leu Ala Gln Lys Val Ala Arg Thr Leu Pro Asp Val Thr
                20                  25                  30

Ala Val Thr Phe Asp Leu Ile
            35
```

(2) INFORMATION FOR SEQ ID NO:27:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
ATATCGGGTA CATACTATCG ATCGTGACAA GGATTAAACT CTCCTCTAGA AGTTCAAAAC        60

CGAGTTTTCC AACGAGCCTG AGAAGGACTG CAGTGTCGTC ATTGAAAACT GAATTAG         117
```

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..17

(xi) SEQUENCE DESCRIPTION: SEQ ID NO:28:

```
CT AGC ACT CCT CCT GCT                                                 17
   Ser Thr Pro Pro Ala
    40
```

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:29:

```
Ser Thr Pro Pro Ala
 1               5

(2) INFORMATION FOR SEQ ID NO:30:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GTGAGGAGGA CGA                                                    13

(2) INFORMATION FOR SEQ ID NO:31:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..12

(xi) SEQUENCE DESCRIPTION: SEQ ID NO:31:

CCA TTT TCA GAC GT                                                14
Pro Phe Ser Asp (2) INFORMATION FOR SEQ ID NO:32:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:32:

Pro Phe Ser Asp
 1

(2) INFORMATION FOR SEQ ID NO:33:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GGTAAAAGTC                                                        10

(2) INFORMATION FOR SEQ ID NO:34:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(ix) FEATURE:
```

(A) NAME/KEY: CDS
            (B) LOCATION: 1..57

(xi) SEQUENCE DESCRIPTION: SEQ ID NO:34:

GTT CCT AAT TTG AGA GGA GAT CTT CAA GTT TTG GCT CAA AAG GTT GCT     48
Val Pro Asn Leu Arg Gly Asp Leu Gln Val Leu Ala Gln Lys Val Ala
 5                  10                  15                  20

CGG ACT CTT                                                         57
Arg Thr Leu (2) INFORMATION FOR SEQ ID NO:35:

(i) SEQUENCE CHARACTERISTICS:
            (A) LENGTH: 19 amino acids
            (B) TYPE: amino acid
            (D) TOPOLOGY: linear (ii) MOLECULE TYPE: protein (xi) SEQUENCE DESCRIPTION: SEQ ID NO:35:

Val Pro Asn Leu Arg Gly Asp Leu Gln Val Leu Ala Gln Lys Val Ala
 1               5                  10                  15

Arg Thr Leu (2) INFORMATION FOR SEQ ID NO:36:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

CAAGGATTAA ACTCTCCTCT AGAAGTTCAA AACCGAGTTT TCCAACGAGC CTGAGAA     57

(2) INFORMATION FOR SEQ ID NO:37:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..42

(xi) SEQUENCE DESCRIPTION: SEQ ID NO:37:

AAA GAT GCT ACT GGA ATC GAT AAT CAT AGA GAA GCA AAA TTG              42
Lys Asp Ala Thr Gly Ile Asp Asn His Arg Glu Ala Lys Leu
 20                  25                  30

(2) INFORMATION FOR SEQ ID NO:38:

(i) SEQUENCE CHARACTERISTICS:
            (A) LENGTH: 14 amino acids
            (B) TYPE: amino acid
            (D) TOPOLOGY: linear (ii) MOLECULE TYPE: protein (xi) SEQUENCE DESCRIPTION: SEQ ID NO:38:

Lys Asp Ala Thr Gly Ile Asp Asn His Arg Glu Ala Lys Leu
 1               5                  10

(2) INFORMATION FOR SEQ ID NO:39:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
TTTCTACGAT GACCTTAGCT ATTAGTATCT CTTCGTTTTA AC                          42
```

(2) INFORMATION FOR SEQ ID NO:40:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..66

(xi) SEQUENCE DESCRIPTION: SEQ ID NO:40:

```
CCT AGA GGA CCA GAC AGA CCT GAA GGA ATA GAA GAG GAA GGT GGA GAA         48
Pro Arg Gly Pro Asp Arg Pro Glu Gly Ile Glu Glu Glu Gly Gly Glu
 15                  20                  25                  30

CGC GAT CGA GAT AGA TCA                                                 66
Arg Asp Arg Asp Arg Ser
                35
```

(2) INFORMATION FOR SEQ ID NO:41:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:41:

```
Pro Arg Gly Pro Asp Arg Pro Glu Gly Ile Glu Glu Glu Gly Gly Glu
 1               5                  10                  15

Arg Asp Arg Asp Arg Ser
            20
```

(2) INFORMATION FOR SEQ ID NO:42:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
GGATCTCCTG GTCTGTCTGG ACTTCCTTAT CTTCTCCTTC CACCTCTTGC GCTAGCTCTA       60

TCTAGT                                                                  66
```